(12) United States Patent
Hwang et al.

(10) Patent No.: US 10,470,664 B2
(45) Date of Patent: Nov. 12, 2019

(54) MOBILE-BASED SPECTRUM IMAGING DEVICE AND METHOD FOR CONTROLLING SAME

(71) Applicant: DAEGU GYEONGBUK INSTITUTE OF SCIENCE AND TECHNOLOGY, Daegu (KR)

(72) Inventors: Jae Youn Hwang, Daegu (KR); Se Hyo Youn, Daegu (KR)

(73) Assignee: Daegu Gyeongbuk Institute of Science and Technology, Daegu (KR)

( * ) Notice: Subject to any disclaimer, the term of this patent is extended or adjusted under 35 U.S.C. 154(b) by 44 days.

(21) Appl. No.: 15/738,116

(22) PCT Filed: Jun. 20, 2016

(86) PCT No.: PCT/KR2016/006506
§ 371 (c)(1),
(2) Date: Dec. 19, 2017

(87) PCT Pub. No.: WO2016/208917
PCT Pub. Date: Dec. 29, 2016

(65) Prior Publication Data
US 2018/0192879 A1    Jul. 12, 2018

(30) Foreign Application Priority Data
Jun. 22, 2015  (KR) .................. 10-2015-0088581

(51) Int. Cl.
*G01J 3/00*     (2006.01)
*A61B 5/00*     (2006.01)
(Continued)

(52) U.S. Cl.
CPC ............ *A61B 5/0075* (2013.01); *A61B 5/441* (2013.01); *A61B 5/6898* (2013.01); *G01J 3/0218* (2013.01);
(Continued)

(58) Field of Classification Search
CPC ........ G01J 3/02; G01J 3/28; G01J 3/10; G01J 3/50; G01N 21/64; G01N 21/59;
(Continued)

(56) References Cited

U.S. PATENT DOCUMENTS

2004/0007675 A1*  1/2004  Gillispie .............. G01J 3/4406
                                                    250/458.1
2005/0033127 A1*  2/2005  Ciurczak ............ A61B 5/14532
                                                    600/316

FOREIGN PATENT DOCUMENTS

JP       2004-302047 A     10/2004
JP       2005-077964 A      3/2005
(Continued)

OTHER PUBLICATIONS

International Search Report and Written Opinion, International Application No. PCT/KR2016/006506, dated Oct. 10, 2016, 15 pages.

*Primary Examiner* — Abdullahi Nur
(74) *Attorney, Agent, or Firm* — Quarles & Brady LLP (57) ABSTRACT

The present invention provides a mobile-based spectrum imaging device and a method for controlling the same. A mobile-based spectrum imaging device according to an embodiment of the present invention may comprise: an optical fiber for emitting, in a beam form, light which has been collected from a light source; a linear filter which is movably installed, divides the light emitted from the optical fiber into particular wavelength bands, and makes the divided light have a wavelength band changing according to the incidence location of the light; and a control unit for controlling the location of the linear filter such that the location of incident light is changed on the linear filter.

19 Claims, 6 Drawing Sheets

(51) Int. Cl.
  *G01J 3/28* (2006.01)
  *G01J 3/12* (2006.01)
  *G01J 3/26* (2006.01)
  *G01J 3/32* (2006.01)
  *G01J 3/02* (2006.01)
  *A61B 17/00* (2006.01)

(52) U.S. Cl.
  CPC ............ *G01J 3/0229* (2013.01); *G01J 3/0272* (2013.01); *G01J 3/12* (2013.01); *G01J 3/26* (2013.01); *G01J 3/28* (2013.01); *G01J 3/32* (2013.01); *A61B 5/0082* (2013.01); *A61B 2017/00061* (2013.01); *G01J 2003/1213* (2013.01); *G01J 2003/1221* (2013.01)

(58) Field of Classification Search
  CPC ........ G01N 27/44; G03B 21/20; G02B 6/293; G02B 6/34; G02B 6/28; F21V 9/16; A61B 5/00
  See application file for complete search history.

(56) References Cited

FOREIGN PATENT DOCUMENTS

| | | |
|---|---|---|
| KR | 10-2012-0001533 A | 1/2012 |
| KR | 10-2012-0015227 A | 2/2012 |
| KR | 10-2013-0106985 A | 10/2013 |

\* cited by examiner

MOBILE-BASED SPECTRUM IMAGING DEVICE AND METHOD FOR CONTROLLING SAME

CROSS-REFERENCE TO RELATED APPLICATIONS

This application is a national stage entry of International Application No. PCT/KR2016/006506, filed on Jun. 20, 2016, which claims priority to Korean Application No. 10-2015-0088581, filed on Jun. 22, 2015, both of which are hereby incorporated by reference in their entirety.

TECHNICAL FIELD

Example embodiments relate to a mobile-based spectral imaging device and a method of controlling the mobile-based spectral imaging device, and more particularly, to a device configured to provide a spectral image with respect to a light source including a plurality of wavelengths and a method of controlling the device.

BACKGROUND ART

In general, spectral imaging and spectral image analysis technology may be used in various fields of applications, for example, checking a health condition and diagnosing a disease, and also bio applications. Such a spectral imaging technology is verified for its effectiveness in diagnosis of skin-related diseases, for example, skin cancer and otitis media, and commercialization thereof is in progress.

However, in existing spectral imaging technology, a light source for image acquisition and a filter for spectral filtering of the light source are classified by each specific bandwidth, and thus they need to be purchased individually for each bandwidth and also a volume of an entire spectral imaging system may thus increase depending on the number of filters.

DISCLOSURE OF INVENTION

Technical Goals

Example embodiments provide a device that may improve spectral decomposition performance without increasing a volume of an entire spectral system, and a method of controlling the device.

Technical Solutions

According to example embodiments described herein, there is provided a mobile-based spectral imaging device, and a method of controlling the mobile-based spectral imaging device.

According to an example embodiment, there is provided a mobile-based spectral imaging device including an optical fiber configured to emit, in a beam form, light collected from a light source, a linear filter movably installed and configured to spectrally divide the light emitted from the optical fiber into a wavelength band, and a controller configured to control a location of the linear filter such that a location of incident light in the linear filter changes. Here, the wavelength band of the spectral light may change based on the location of the incident light.

A size of the light in the beam form may be determined based on an inner diameter of a core of the optical fiber.

The mobile-based spectral imaging device may further include a size processing hole filter disposed between the optical fiber and the linear filter, and configured to change the size of the light in the beam form transmitted along an inner diameter of a hole of the size processing hole filter.

The mobile-based spectral imaging device may further include a wavelength controlling hole filter disposed on a path of light emitted from the linear filter, and configured to control a center wavelength by transmitting a portion of the spectral light through the wavelength controlling hole filter.

The linear filter may be installed to be movable along a length direction.

The mobile-based spectral imaging device may further include a driver configured to apply power required for moving the location of the linear filter.

The driver may include a motor.

The controller may determine a location in the linear filter to which light is to be emitted based on a control command received from an external control device.

The light may be collected by the optical fiber from the light source included in the control device.

The controller may determine the location to which the light in the beam form is to be emitted by controlling the driver based on the control command.

The mobile-based spectral imaging device may further include a lens configured to expand a range of the spectral light from the linear filter and emit light with the expanded range to an object.

The lens may include at least one concave lens.

The controller may control the location to which the light in the beam form is to be emitted and a reference point of the linear filter to correspond to each other.

According to another example embodiment, there is provided a method of controlling a mobile-based spectral imaging device, the method including collecting, using an optical fiber, light emitted in a beam form from a light source, emitting, to a linear filter, light emitted through the optical fiber, and moving the linear filter to allow light transmitted from the linear filter to be spectrally divided into a wavelength band.

A size of the light in the beam form may be determined based on an inner diameter of a core of the optical fiber.

The size of the light in the beam form may be determined based on an inner diameter of a hole of a size processing hole filter disposed between the optical fiber and the linear filter.

The method may further include controlling a center wavelength of light to be transmitted by transmitting only a portion of the light transmitted from the linear filter.

The controlling of the center wavelength of the light may include emitting a portion of the spectral light by transmitting, through a wavelength controlling hole filter, the light transmitted from the linear filter.

The moving of the linear filter may include linearly changing a spectrum of the light transmitted from the linear filter by controlling a location of the linear filter.

The moving of the linear filter may include moving the linear filter along a length direction.

The moving of the linear filter may include determining a location in the linear filter to which light is to be emitted based on a control command received from a control device connected to the mobile-based spectral imaging device.

The light may be collected from the light source included in the control device.

The moving of the linear filter may include controlling a motor based on the control command.

The method may further include transmitting, to a lens, a portion of the spectral light to be expanded, and emitting the expanded light to an object.

The lens may include at least one concave lens.

The emitting of the light emitted through the optical fiber to the linear filter may include controlling a location to which the light transmitted from the linear filter is to be emitted and a reference point of the linear filter to correspond to each other.

Advantageous Effects

According to example embodiments described herein, there is provided a mobile-based spectral imaging device. By determining a size of a beam emitted to a linear spectral filter using an optical fiber, a structure of the mobile-based spectral imaging device may be simplified.

In addition, by providing a continuous spectrum through the linear spectral filter, spectral decomposition performance may be improved. Also, by reducing the number of filters to be used to obtain a spectral image, an entire system may be reduced in size.

Further, using a mobile device such as a smartphone as a control device, devices such as an input device, a display, and a light source may be stably secured, thereby enhancing general usability and device compatibility.

BEST MODE FOR CARRYING OUT THE INVENTION

The following detailed description is provided to assist the reader in gaining a comprehensive understanding of the methods, apparatuses, and/or systems described herein. However, various changes, modifications, and equivalents of the methods, apparatuses, and/or systems described herein will be apparent after an understanding of the disclosure of this application. For example, the sequences of operations described herein are merely examples, and are not limited to those set forth herein, but may be changed as will be apparent after an understanding of the disclosure of this application, with the exception of operations necessarily occurring in a certain order. Also, descriptions of features that are known in the art may be omitted for increased clarity and conciseness. The features described herein may be embodied in different forms, and are not to be construed as being limited to the examples described herein. Rather, the examples described herein have been provided merely to illustrate some of the many possible ways of implementing the methods, apparatuses, and/or systems described herein that will be apparent after an understanding of the disclosure of this application.

Throughout the disclosure, the terms "and/or" and "at least one" may include any one and any combination of any two or more of the associated listed items. For example, "A and/or B" and "at least one of A or B" may include one of A and B, or include both A and B.

Although terms such as "first," "second," and the like may be used herein to describe various members, components, regions, layers, or sections, these members, components, regions, layers, or sections are not to be limited by these terms. Rather, these terms are only used to distinguish one member, component, region, layer, or section from another member, component, region, layer, or section. Thus, a first member, component, region, layer, or section referred to in examples described herein may also be referred to as a second member, component, region, layer, or section without departing from the teachings of the examples.

Throughout the disclosure, when an element, such as a layer, region, or substrate, is described as being "on," "connected to," or "coupled to" another element, it may be directly "on," "connected to," or "coupled to" the other element, or there may be one or more other elements intervening therebetween. In contrast, when an element is described as being "directly on," "directly connected to," or "directly coupled to" another element, there can be no other elements intervening therebetween.

The terminology used herein is for describing various examples only, and is not to be used to limit the disclosure. The articles "a," "an," and "the" are intended to include the plural forms as well, unless the context clearly indicates otherwise. The terms "comprises," "includes," and "has" specify the presence of stated features, numbers, operations, members, elements, and/or combinations thereof, but do not preclude the presence or addition of one or more other features, numbers, operations, members, elements, and/or combinations thereof.

It is obvious that an apparatus or device, or an electronic apparatus or device, according to various example embodiments of the present disclosure may be replaced with a same form or type of apparatuses or devices or other similar forms or types of apparatuses or devices unless the apparatus or the device is defined by certain limited specifications. For example, when a smartphone is provided as an example of the apparatus or device, it is obvious that the smartphone may be replaced with a smart pad or a note pad with a same or similar function and/or configuration as or to the smartphone. For another example, when a wristband is provided as an example of the apparatus or device, it is obvious that the wristband may be replaced with one of various apparatuses described herein or a combination thereof.

Hereinafter, an electronic device will be described according to various example embodiments with reference to the accompanying drawings. In the example embodiments, the term "user" refers to a person who uses the electronic device, or a device or an apparatus that uses the electronic device, for example, an artificial intelligence-based electronic device. Further, the electronic device may be attached to or worn around or on a part of a body of the user, and the user is also referred to as a user or a wearer while the electronic device is being attached to or worn around or on the part of the body. In such a case in which the electronic device is attached to or worn around or on the part of the body, the electronic device is also referred to as a wearable electronic device, or a wearable device.

Figure 1:
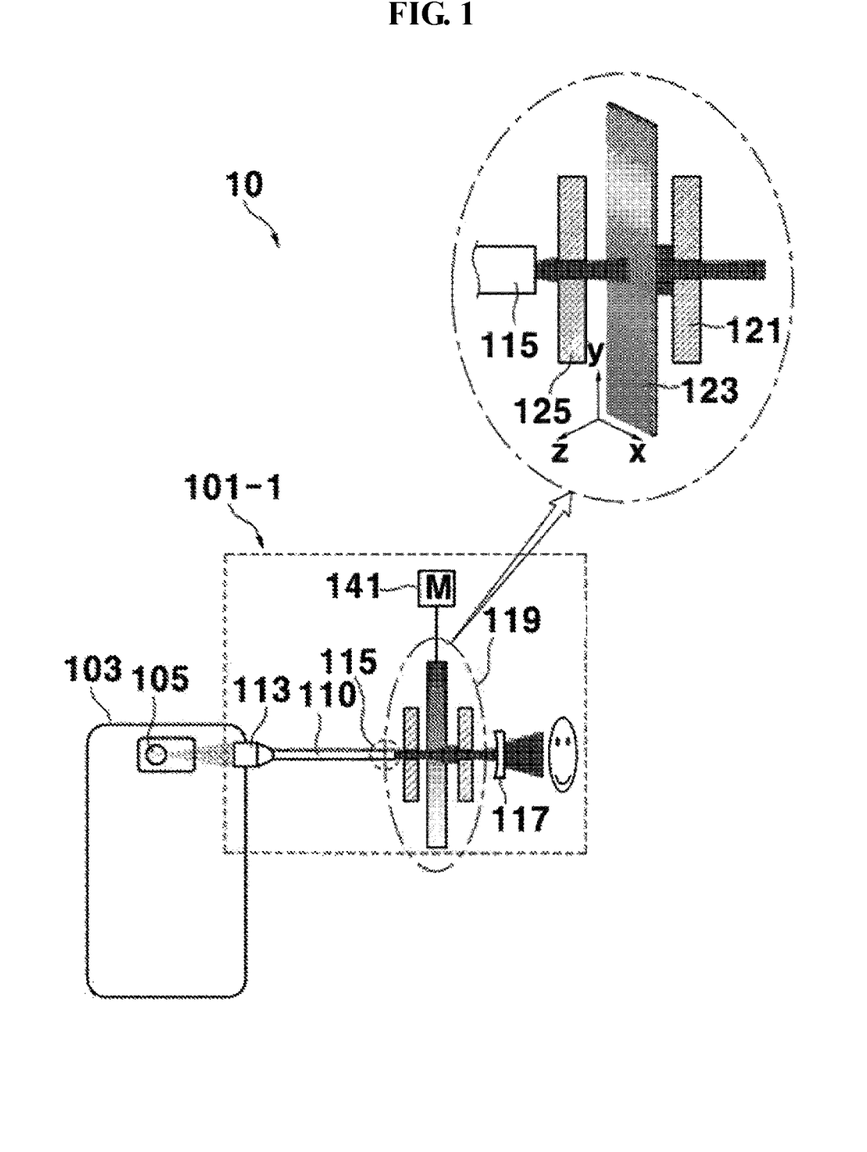
FIG. 1 is a diagram illustrating an example of a system including a mobile-based spectral imaging device according to an example embodiment.

FIG. 1 is a diagram illustrating an example of a system including a mobile-based spectral imaging device according to an example embodiment.

Referring to FIG. 1, a mobile-based spectral imaging system 10 includes a mobile-based spectral imaging device 101-1, and a control device 103 configured to provide light to the mobile-based spectral imaging device 101-1 and control the mobile-based spectral imaging device 101-1.

According to an example embodiment, the mobile-based spectral imaging device 101-1 may spectrally process light received or collected from a light source 105 of the control device 103 using a linear variable filter or a linear spectral filter (hereinafter simply referred to as a linear filter 123), and emit the spectrally processed light, or also referred to as spectral light. The linear filter 123 may linearly change a spectrum of transmitted light in response to a linear change in a location of incident light. A linear variable bandpass filter, which is an example of the linear filter 123, may be a coated optical filter having a spectral characteristic that varies linearly over an entire filter length. The linear variable bandpass filter may have a high transmissivity in a narrow bandwidth and a deep blocking performance for undesired light, and thus may maximize system performance at a required wavelength. Thus, it is possible to adjust a spectral response only by changing a location of the linear filter 123 based on a location of incident light. A linear variable edge filter, which is another example of the linear filter 123, may also be used individually or in pairs to selectively block or transmit a specific wavelength. The linear variable edge filter may be used as a longpass filter, a shortpass filter, or a dichroic filter. A longpass edge filter may transmit a wavelength longer than a cut-on wavelength, whereas a shortpass edge filter may transmit a wavelength shorter than a cut-off wavelength. A dichroic edge filter may have a similar characteristic to that of the longpass edge filter, and reflect an undesired wavelength. That is, in a case in which at least two thereof is used in combination as the linear variable edge filter, it may function as a laser line filter or a variable bandpass filter, and adjust a center wavelength and a bandwidth.

In a structure of the mobile-based spectral imaging device 101-1, a light inputter configured to receive light from the light source 105 is provided as an optical fiber 110. The optical fiber 110 may emit, to the linear filter 123, the light received from the light source 105. To collect light emitted from the light source 105, at least one lens 113, for example, a condensing lens, is attached to an end of the optical fiber 110 in a direction of the light source 105. An intensity of light output from the optical fiber 110 may be determined based on a diffraction limit of the lens 113 attached to the optical fiber 110. Light received through the lens 113 may be output, in a beam form, to an end 115 of the optical fiber 110 in a direction of the linear filter 123.

Light emitted from the end 115 of the optical fiber 110 may be emitted to the linear filter 123 through a processing hole filter 125, or a size processing hole filter, of a filter portion 119. The processing hole filter 125 may process a size of the light in the beam form that is emitted from the optical fiber 110 based on an inner diameter of a hole thereof. Subsequently, the processed light may be spectrally filtered or divided through the linear filter 123 to be emitted to a wavelength controlling hole filter 121. The linear filter 123 may be designed to allow a center wavelength of light transmitted through the linear filter 123 to be linearly changed based on a change in a location to which light is to be emitted. For example, in a case in which the location of the linear filter 123 to which the light processed through the processing hole filter 125 is to be emitted is changed, a center wavelength of light to be transmitted may be determined based on the changed location. According to an example embodiment, the center wavelength of the light transmitted through the linear filter 123 from the light emitted through the processing hole filter 125 may be linearly changed when the location of the linear filter 123, for example, a value on a y axis of the linear filter 123 as illustrated in FIG. 1, is changed.

A range of a center wavelength of the spectral light that is obtained by spectral filtering through the linear filter 123 may be determined through the wavelength controlling hole filter 121. For example, the spectral light obtained through the linear filter 123 may be divided into various wavelengths based on a filter characteristic. The range of the center wavelength of the spectral light to be output may be determined based on an inner diameter of a hole of the wavelength controlling hole filter 121. As described above, a range of a wavelength of light that is finally output from the spectral light may be controlled by controlling the inner diameter of the hole of the wavelength controlling hole filter 121. Here, a concave lens 117, which is disposed at an output end of the filter portion 119, may expand a range of light to be emitted to an object.

According to example embodiments described herein, there is provided a method and device to change the location of the linear filter 123 included in the filter portion 119. For example, the linear filter 123 may be connected to a motor 141 and move based on an operation of the motor 141, or a value on a y axis of the linear filter 123 as illustrated in FIG. 1 may move. Here, the motor 141 may move the linear filter 123 based on control information received from the control device 103. In detail, each of the mobile-based spectral imaging device 101-1 and the control device 103 may include a communicator, and the mobile-based spectral imaging device 101-1 may receive the control information to move the motor 141 from the control device 103 through the communicator thereof. The control information may include, for example, coordinate information about coordinates to which the linear filter 123 is to move. The motor 141 may determine the movement of the linear filter 123 based on the received control information. The control information may be data or a packet in a format used for communication with the control device 103. It is obvious that the definition of the control device 103 described in the foregoing may be applicable to FIG. 1 and descriptions to be provided hereinafter. For example, the control device 103 may be a smartphone including a communicator and a light source, for example, a flash.

Figure 2:
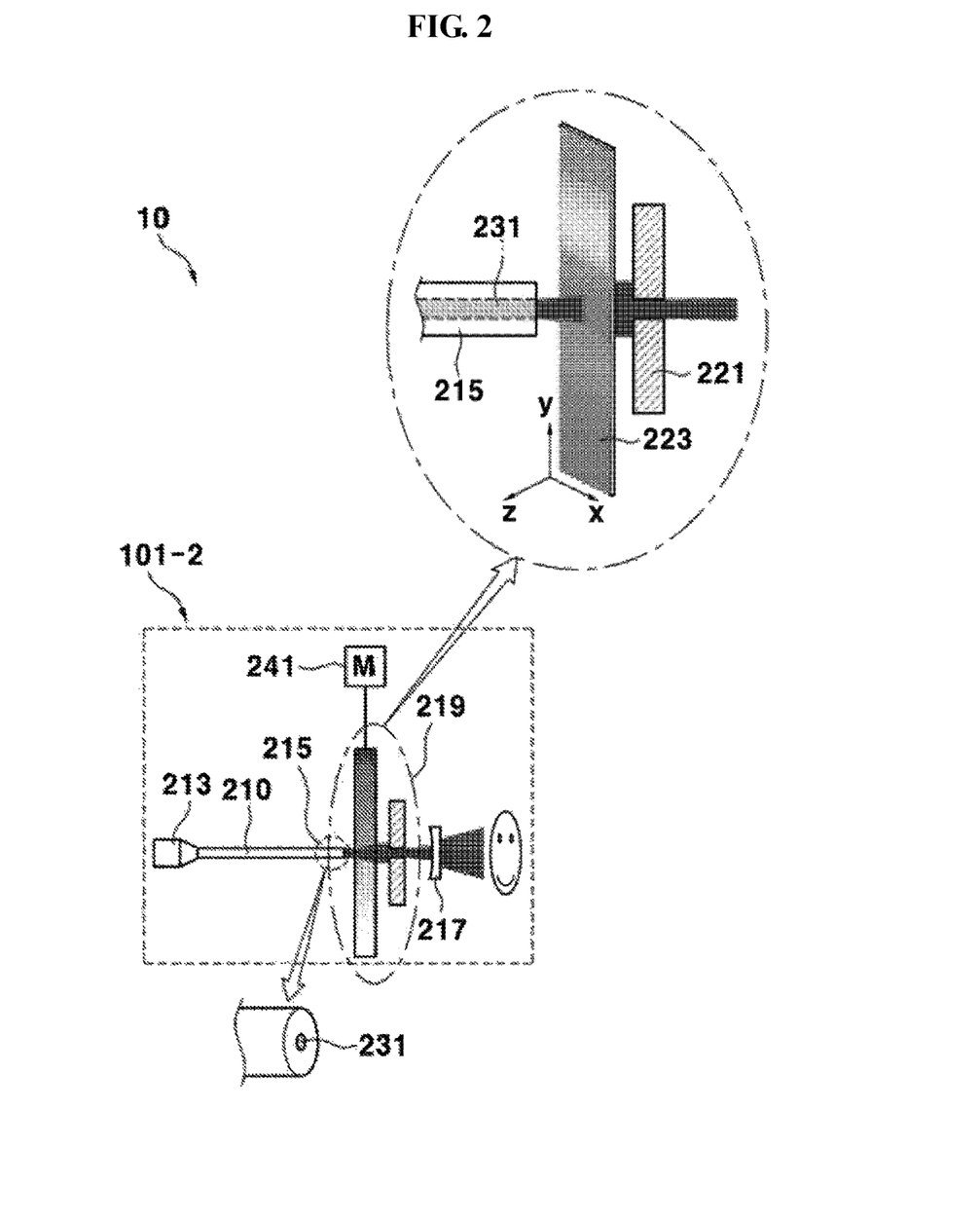
FIG. 2 is a diagram illustrating another example of a system including a mobile-based spectral imaging device according to another example embodiment.

FIG. 2 is a diagram illustrating another example of a system including a mobile-based spectral imaging device according to another example embodiment.

Referring to FIG. 2, a filter portion 219 of a mobile-based spectral imaging device 101-2 is a partial modification to the filter portion 119 illustrated in FIG. 1. For example, the filter portion 219 may be obtained by removing the processing hole filter 125 from the filter portion 119 of FIG. 1. In detail, the filter portion 219 includes a linear filter 223 configured to spectrally filter light emitted from an end 215 of an optical fiber 210, and a wavelength controlling hole filter 221.

According to an example embodiment, the filter portion 119 of FIG. 1 may process a size of light in a beam form that is emitted from the optical fiber 110 through the processing hole filter 125, and emit the processed light to the linear filter 123. The filter portion 219 of FIG. 2 may determine a size of light in a beam form to be emitted to the linear filter 223 based on the optical fiber 210. For example, the size of the light in the beam form to be emitted to the linear filter 223 may be determined based on an inner diameter of a core 231 of the optical fiber 210. That is, the mobile-based spectral imaging device 101-2 may selectively apply an optical fiber among optical fibers having different inner diameters, and control the size of the light in the beam form to be emitted to the linear filter 210 based on an inner diameter of a core of the applied optical fiber. Here, the size and an intensity of the light in the beam form to be output from the optical fiber 210 may be determined based on a diffraction limit of a lens 213 attached to the optical fiber 210 and/or the inner diameter of the core 231 of the optical fiber 210.

Thus, the mobile-based spectral imaging device 101-2 may be configured more compactly by collecting light emitted from a light source and simultaneously adjusting a size of the light using only a single optical fiber, for example, the optical fiber 210, without an additional processing hole filter as illustrated in FIG. 2.

Figure 3:
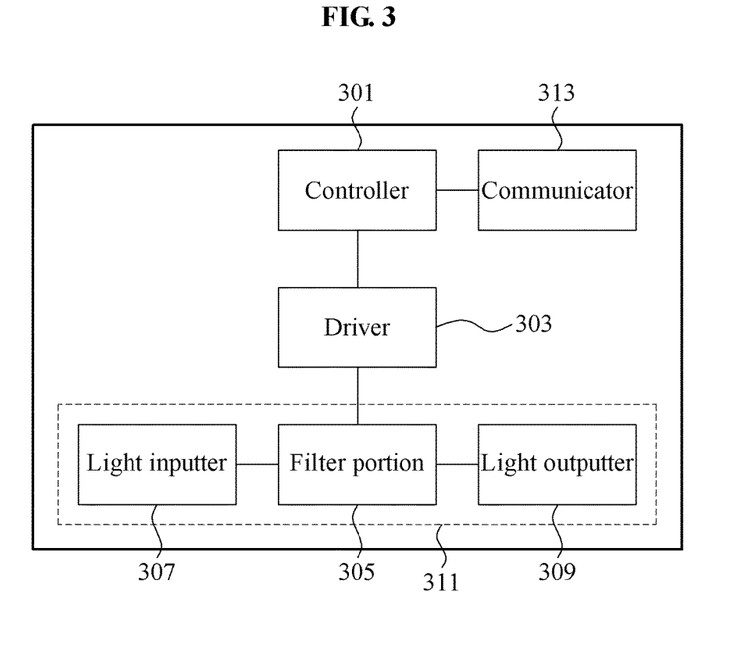
FIG. 3 is a block diagram illustrating a mobile-based spectral imaging device according to an example embodiment.

FIG. 3 is a block diagram illustrating a mobile-based spectral imaging device according to an example embodiment.

According to an example embodiment, a mobile-based spectral imaging device 101 includes at least one of a controller 301, a driver 303, an optical portion 311, or a communicator 313. The mobile-based spectral imaging device 101 described herein may collectively indicate the mobile-based spectral imaging device 101-1 of FIG. 1 and the mobile-based spectral imaging device 101-2 of FIG. 2, unless otherwise specified.

The controller 301 may control a location of a linear filter included in a filter portion 305 through the driver 303. For example, the controller 301 may receive at least one piece of control information through the communicator 313. The received control information may include at least one piece of location information. The location information included in the control information may be coordinate information of the linear filter included in the filter portion 305. The controller 301 may control the location of the linear filter to move or change through the driver 303 based on the location information. For example, the controller 301 may verify the coordinate information, and or a control command, included in the control information received through the communicator 313. The controller 301 may control the driver 303 to move the linear filter in a coordinate system set for the linear filter based on the coordinate information. For example, based on the coordinate system of the linear filter, at least one coordinate may be set at the location of the linear filter that passes through a specific wavelength.

The driver 303 may include at least one motor, for example, the motor 141 of FIG. 1 or the motor 241 of FIG. 2, and move the linear filter included in the filter portion 305 by driving the motor based on the control information received from the controller 301. The moving of the linear filter may indicate a parallel translation in a y-axis direction and/or an x-axis direction in a coordinate system set for the linear filter 123 of FIG. 1.

The optical portion 311 may include at least one of a light inputter 307, the filter portion 305, or a light outputter 309. Referring back to FIG. 1, the light inputter 307 may include the lens 113 and/or the optical fiber 110, the filter portion 305 may include at least one of the wavelength controlling hole filter 121 or the processing hole filter 125 and/or the linear filter 123, and the light outputter 309 may include the concave lens 117.

The lens 113 of the light inputter 307 may collect light from the light source 105 and transmit the collected light to the optical fiber 110, and emit light in a beam form through an end of the optical fiber 110, for example, the end 115 of FIG. 1. A size of the light emitted from the end of the optical fiber 110 may be processed through a processing hole filter of the filter portion 305, for example, the processing hole filter 125 of FIG. 1, and the processed light may be emitted to the linear filter 123. Here, in a case in which the processing hole filter 125 is removed from the filter portion 119 of FIG. 1, the size of the light in the beam form to be emitted to the linear filter 123 may be determined based on a diameter of a core of the optical fiber 110, for example, the core 231. For example, as illustrated in FIG. 2, a size of light in a beam form to be emitted to the filter portion 219 may be determined based on a diameter of the core 231 of the optical fiber 210.

The filter portion 305 may include the linear filter configured to spectrally filter light to be emitted, and at least one hole filter. In a case in which a processing hole filter is provided at an end of an optical fiber, a size of light in a beam form to be emitted to the linear filter may be processed and determined through the processing hole filter provided at the end of the optical fiber. Alternatively, in a case in which the processing hole filter is not disposed at the end of the optical fiber, the size of the light in the beam form to be emitted to the linear filter may be determined based on a diameter of a core of the optical fiber.

The linear filter of the filter portion 305 may spectrally filter light emitted from the optical fiber or the processing hole filter at the end of the optical fiber. The linear filter may be connected to at least one motor included in the driver 303 and move based on the control information from the controller 301. For example, a coordinate system may be set for the linear filter of the filter portion 305. The motor of the driver 303 may move the linear filter such that the light emitted from the optical fiber may be emitted to coordinates determined by the controller 301. Here, only a center wavelength in a preset range of the light that is spectrally filtered or divided through the linear filter, for example, a spectrum, may be emitted to the light outputter 309 through a wavelength controlling hole filter disposed at an output end of the linear filter. Here, the range of the center wavelength of the light to be emitted to the light outputter 309 may be determined based on an inner diameter of a hole of the wavelength controlling hole filter disposed at the output end of the linear filter.

The light emitted to the light outputter 309, for example, spectral light or spectrum, may be expanded based on a refractive index of a concave lens and externally emitted from the mobile-based spectral imaging device 101.

The communicator 313 may be connected to a communicator included in at least one control device, for example, the control device 103 of FIG. 1, and exchange data with the communicator of the control device. For example, the communicator 313 may receive control information from the communicator of the control device 103, and feed, back to the control device 103, a result of moving the linear filter based on the control information by the controller 301. The communicator 313 may be connected to the communicator included in the control device 103 through wireless communication and/or wired communication. In a case of the wireless communication being used, the wireless communication may include at least one of wireless fidelity (WiFi) communication, Bluetooth low energy (BLE) communication, Bluetooth (BT) communication, near field communication (NFC), a global positioning system (GPS), or cellular communication, for example, LTE, LTE-A, CDMA, WCDMA, UMTS, WiBro, and GSM. In a case of the wired communication being used, the wired communication may include at least one of a universal serial bus (USB), a high definition multimedia interface (HDMI), a recommended standard 232 (RS-232), or a plain old telephone service (POTS).

Figure 4:
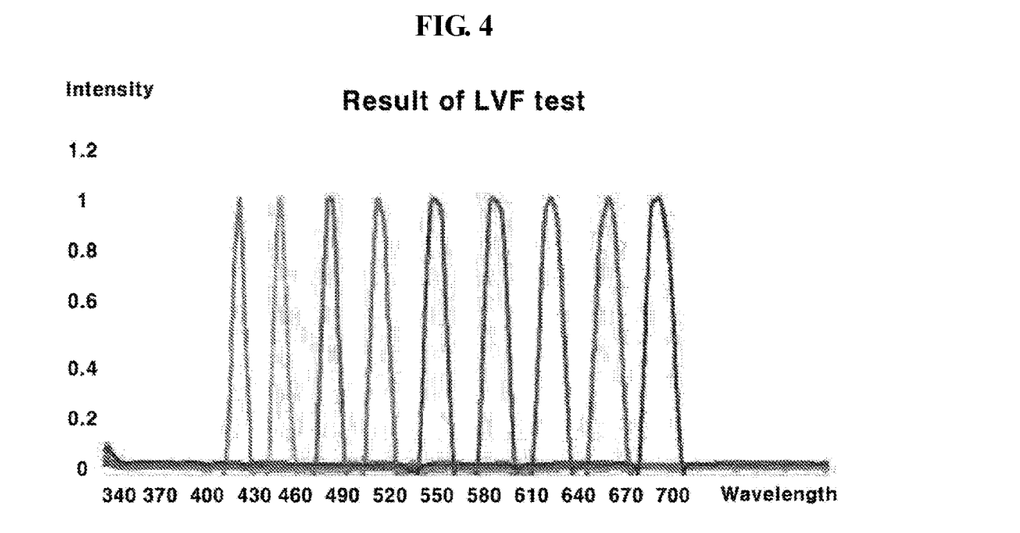
FIG. 4 is a diagram illustrating an example of a spectrum of light spectrally divided or filtered through a linear filter of a mobile-based spectral imaging device according to an example embodiment.

FIG. 4 is a diagram illustrating an example of a spectrum of light spectrally filtered or divided through a linear filter of a mobile-based spectral imaging device according to an example embodiment. Referring to FIG. 4, it is possible to provide an effect of replacing a plurality of bandpass filters by changing a location, for example, coordinates, of a linear filter to which light is to be emitted based on a coordinate system set for the linear filter as described with reference to FIG. 3.

Figure 5:
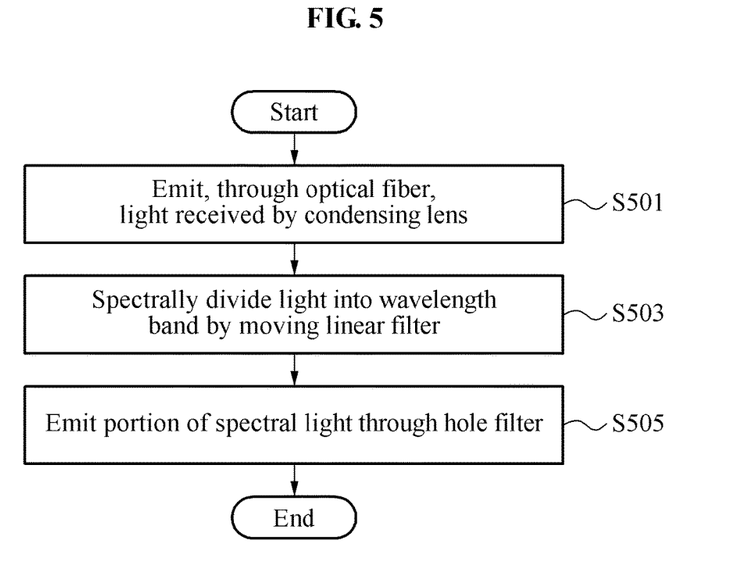
FIG. 5 is a flowchart illustrating a method of controlling a mobile-based spectral imaging device according to an example embodiment.

FIG. 5 is a flowchart illustrating a method of controlling a mobile-based spectral imaging device according to an example embodiment.

In operation S501, the mobile-based spectral imaging device 101 emits, through an optical fiber, light received by a condensing lens. For example, referring back to FIG. 1, the lens 113 may collect light emitted from the light source 105 and transmit the collected light to the optical fiber 110. Here, an intensity of the light to be emitted to the end 115 of the optical fiber 110 may be determined based on a diffractive limit of the lens 113 attached to the optical fiber 110 and/or an inner diameter of a core of the optical fiber 110. Also, a size of light in a beam form to be emitted may be determined based on an inner diameter of a hole of the processing hole filter 125 when the processing hole filter 125 is disposed at the end 115 of the optical fiber 110 as shown in the filter portion 119 of FIG. 1, or based on an inner diameter of the core 231 of the optical fiber 210 when such a processing hole filter is not disposed at the end 215 of the optical fiber 210 as shown in the filter portion 219 of FIG. 2.

In operation S503, the mobile-based spectral imaging device 101 spectrally processes the light emitted to the linear filter to be light with a specific wavelength, using the linear filter. For example, referring back to FIG. 1, light output to the end 115 of the optical fiber 110 may be emitted to the linear filter 123. In such an example, a location to which the light is to be emitted may be fixed, and a location of the linear filter 123 may be moved or changed in response to an operation of the motor 141 while the linear filter 123 is being connected to the motor 141. Based on a filter characteristic, the linear filter 123 may transmit light of a specific wavelength band.

In operation S505, the mobile-based spectral imaging device 101 selectively emits a portion of a center wavelength of the light of the specific wavelength band that is emitted from the linear filter. For example, referring back to FIG. 1, a wavelength controlling hole filter may be included at an output end of the linear filter 123 of the filter portion 119, and may transmit the portion of the light of the specific wavelength band that is emitted from the linear filter 123 based on an inner diameter of the wavelength controlling hole filter. A range of light transmitted through the wavelength controlling hole filter may be expanded to be emitted through a concave lens, and the light with the expanded range may be externally emitted from the mobile-based spectral imaging device 101.

After performing operation S505, the mobile-based spectral imaging device 101 may complete performing the method described above with reference to FIG. 5.

Figure 6:
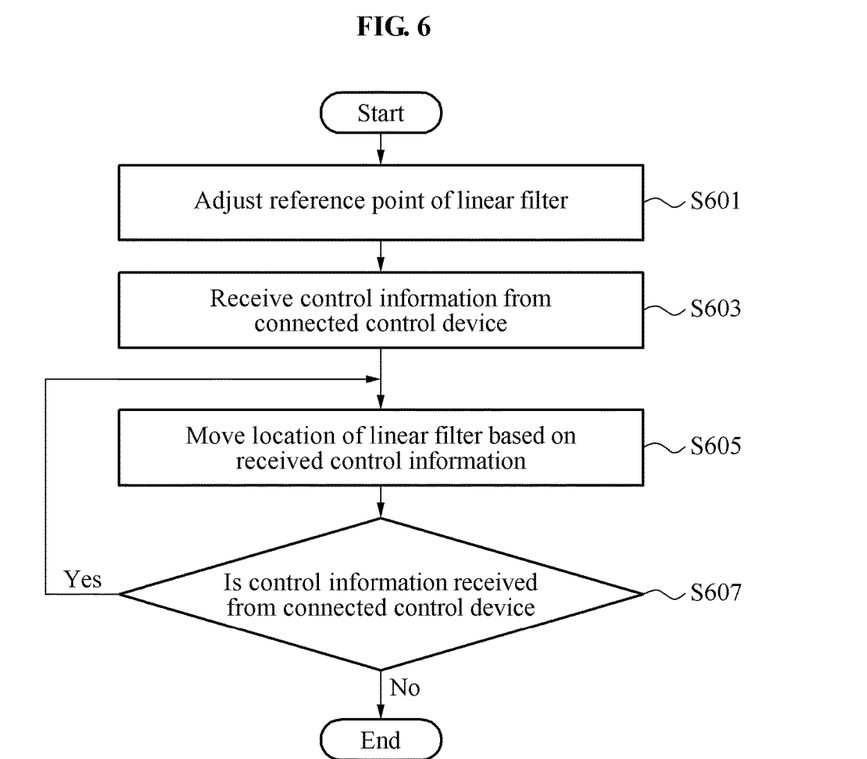
FIG. 6 is a flowchart illustrating a method of controlling a linear filter in a method of controlling a mobile-based spectral imaging device according to an example embodiment.

FIG. 6 is a flowchart illustrating a method of controlling a linear filter in a method of controlling a mobile-based spectral imaging device according to an example embodiment.

In operation S601, the mobile-based spectral imaging device 101 adjusts a reference point of a linear filter, for example, a zero (0) point. For example, the controller 301 of the mobile-based spectral imaging device 101 may verify a zero point in a coordinate system set for the linear filter, for example, the linear filter 123 of FIG. 1, and verify a location or coordinates of the linear filter to which light emitted through an end of an optical fiber is to be emitted. The controller 301 may control the location to which the light is to be emitted and the zero point of the linear filter to correspond to each other. Alternatively, the controller 301 may generate the coordinate system of the linear filter 123 based on the location of the linear filter 123 to which the light is to be emitted. Here, when a coordinate system previously set for the linear filter 123 is present, the controller 301 may correct or change the previously set coordinate system. Operation S601 described above with reference to FIG. 6 may not be necessarily performed. For example, in a case in which a reference point of the linear filter 123 is manually adjusted, the mobile-based spectral imaging device 101 may not perform operation S601, but start performing operations with operation S603.

In operation S603, the mobile-based spectral imaging device 101 receives control information from a control device, for example, the control device 103, that is connected thereto through wired or wireless communication. For example, the mobile-based spectral imaging device 101 may be connected to the control device 103 through Bluetooth communication, and receive the control information including a control command for controlling a motor through at least one program or application interworking with the control device 103.

In operation S605, the mobile-based spectral imaging device 101 verifies the control command in the received control command, and moves a location of the linear filter by controlling the motor based on the verified control command. For example, the mobile-based spectral imaging device 101 may be connected to a communicator included in the control device 103 through wireless communication and/or wired communication. In a case of using the wireless communication, the wireless communication may include at least one of WiFi communication, BLE communication, BT communication, NFC, a GPS, or cellular communication (e.g., LTE, LTE-A, CDMA, WCDMA, UMTS, WiBro, and GSM). In a case of using the wired communication, the wired communication may include at least one of a USB, an HDMI, RS-232, or POTS.

The mobile-based spectral imaging device 101 may obtain the control command to operate the motor of the mobile-based spectral imaging device 101 from a data field of the received control information, and move or change the location of the linear filter based on the obtained control command. The mobile-based spectral imaging device 101 may verify the changed location of the linear filter, and transmit or feed the verified location back to the control device 103.

In operation S607, the mobile-based spectral imaging device 101 verifies whether the control information is received from the control device connected thereto, for example, the control device 103. Operation S607 may be performed to change the location of the linear filter based on the control information received in operation S603, receive the control information to correct the changed location of the linear filter, or change the location of the linear filter to which light emitted from the optical fiber, for example, the optical fiber 110 of FIG. 1, is to be emitted based on the control information.

The mobile-based spectral imaging device 101 may perform operation S605 when the control information is received, and terminate the method described above with reference to FIG. 6 when the control information is not received.

The methods and/or devices described herein may be embodied through at least one of the mobile-based spectral imaging device 101 or the control device 103 as illustrated in FIG. 1, and also be embodied by software programs or applications performing the operations. Such programs may be stored in a computer-readable recording medium or transmitted by a computer data signal combined with a carrier wave in a transmission medium or a communication network.

The computer-readable recording medium may include all types of recording devices or non-transitory computer-readable media, examples of which include a read-only memory (ROM), a random access memory (RAM), a compact disc (CD) ROM, a digital versatile disc (DVD) ROM, and a DVD RAM, and magnetic media such as hard disks, floppy disks, and magnetic tape; magneto-optical media such as floptical disks; optical data storage devices; and hardware devices that are specially configured to store and perform program instructions.

Although a few example embodiments have been shown and described herein, the present disclosure is not limited to the described example embodiments. Instead, it would be appreciated by those skilled in the art that changes may be made to these example embodiments without departing from the principles and spirit of the disclosure, the scope of which is defined by the claims and their equivalents.

The invention claimed is:

1. A mobile-based spectral imaging device, comprising:
   an optical fiber configured to emit, in a beam form, light collected from a light source;
   a linear filter movably installed and configured to spectrally divide the light emitted from the optical fiber into a wavelength band, wherein the wavelength band of the spectral light changes based on a location of incident light;
   a controller configured to control a location of the linear filter such that the location of the incident light in the linear filter changes; and
   a lens configured to expand a range of the spectral light from the linear filter and emit light with the expanded range to an object.

2. The mobile-based spectral imaging device of claim 1, wherein a size of the light in the beam form is determined based on an inner diameter of a core of the optical fiber.

3. The mobile-based spectral imaging device of claim 1, further comprising:
   a size processing hole filter disposed between the optical fiber and the linear filter, and configured to change a size of the light in the beam form transmitted along an inner diameter of a hole thereof.

4. The mobile-based spectral imaging device of claim 1, further comprising:
   a wavelength controlling hole filter disposed on a path of light emitted from the linear filter, and configured to control a center wavelength by transmitting a portion of the spectral light therethrough.

5. The mobile-based spectral imaging device of claim 1, wherein the linear filter is installed to be movable along a length direction.

6. The mobile-based spectral imaging device of claim 1, further comprising:
   a driver configured to apply power required for moving the location of the linear filter.

7. The mobile-based spectral imaging device of claim 6, wherein the driver includes a motor.

8. The mobile-based spectral imaging device of claim 6, wherein the controller is configured to determine a location in the linear filter to which light is to be emitted based on a control command received from an external control device.

9. The mobile-based spectral imaging device of claim 8, wherein the light is collected by the optical fiber from the light source included in the control device.

10. The mobile-based spectral imaging device of claim 8, wherein the controller is configured to determine the location to which the light in the beam form is to be emitted by controlling the driver based on the control command.

11. The mobile-based spectral imaging device of claim 1, wherein the lens includes at least one concave lens.

12. The mobile-based spectral imaging device of claim 1, wherein the controller is configured to control the location to which the light in the beam form is to be emitted and a reference point of the linear filter to correspond to each other.

13. A method of controlling a mobile-based spectral imaging device, the method comprising:
   collecting, using an optical fiber, light emitted in a beam form from a light source;
   emitting, to a linear filter, light emitted through the optical fiber;
   moving the linear filter to allow light transmitted from the linear filter to be spectrally divided into a wavelength band; and
   transmitting, to a lens, a portion of the spectral light to be expanded, and emitting the expanded light to an object.

14. The method of claim 13, wherein a size of the light in the beam form is determined based on at least one of an inner diameter of a core of the optical fiber or an inner diameter of a hole of a size processing hole filter disposed between the optical fiber and the linear filter.

15. The method of claim 13, further comprising:
   controlling a center wavelength of light to be transmitted by transmitting only a portion of the light transmitted from the linear filter.

16. The method of claim 15, wherein the controlling of the center wavelength of the light comprises:
   emitting a portion of the spectral light by transmitting, through a wavelength controlling hole filter, the light transmitted from the linear filter.

17. The method of claim 13, wherein the moving of the linear filter comprises:
   linearly changing a spectrum of the light transmitted from the linear filter by controlling a location of the linear filter.

18. The method of claim 13, wherein the emitting of the light emitted through the optical fiber to the linear filter comprises:
   controlling a location to which the light transmitted from the linear filter is to be emitted and a reference point of the linear filter to correspond to each other.

19. A mobile-based spectral imaging device, comprising:
   a lens configured to collect light from a light source and modify an intensity of the light based on a diffractive limit of the lens;

an optical fiber configured to condense the light emitted from the lens into a beam;

a linear filter moveable relative to the optical fiber and configured to spectrally divide the beam emitted from the optical fiber to produce a wavelength band of spectral light, wherein the wavelength band of the spectral light depends linearly on where the beam strikes along the linear filter;

a first processing hole filter disposed between the optical fiber and the linear filter, and configured to modify a size of the beam based on a first inner diameter of a first hole of the first processing hole filter;

a second processing hole filter configured to output a processed central range of the wavelength band based on a second inner diameter of a second hole of the second processing hole filter; and a controller configured to move the linear filter to a coordinate determined by the controller such that the beam strikes the linear filter at a location along the linear filter determined by the controller.

* * * * *